United States Patent
Dambinova et al.

(10) Patent No.: US 10,408,829 B2
(45) Date of Patent: Sep. 10, 2019

(54) DIAGNOSTIC REAGENT KIT FOR DETECTING CHRONIC BRAIN PATHOLOGIES OF ISCHEMIC GENESIS

(71) Applicant: Obschestvo s ogranichennoi otvetstvennostyu <DRD>, Ulan-Ude (RU)

(72) Inventors: Svetlana Aleksandrovna Dambinova, St. Petersburg (RU); Galina Aleksandrovna Izykenova, St. Petersburg (RU); Alexander Anisimovich Skoromets, St. Petersburg (RU); Evgeny Ivanovich Gusev, Moscow (RU); Mikhail Yuryevich Martynov, Moscow (RU)

(73) Assignee: OBSCHESTVO S OGRANICHENNOI OTVETSTVENNOSTYU «DRD», Ulan-Ude (RU)

( * ) Notice: Subject to any disclaimer, the term of this patent is extended or adjusted under 35 U.S.C. 154(b) by 0 days.

(21) Appl. No.: 16/307,491

(22) PCT Filed: Dec. 20, 2017

(86) PCT No.: PCT/RU2017/000956
§ 371 (c)(1),
(2) Date: Dec. 6, 2018

(87) PCT Pub. No.: WO2019/017811
PCT Pub. Date: Jan. 24, 2019

(65) Prior Publication Data
US 2019/0187133 A1 Jun. 20, 2019

(30) Foreign Application Priority Data
Jul. 18, 2017 (RU) .............................. 2017122628

(51) Int. Cl.
*G01N 33/544* (2006.01)
*C07K 19/00* (2006.01)
*G01N 33/541* (2006.01)
*G01N 33/532* (2006.01)

(52) U.S. Cl.
CPC ........... *G01N 33/544* (2013.01); *C07K 19/00* (2013.01); *G01N 33/532* (2013.01); *G01N 33/541* (2013.01); *G01N 2800/2871* (2013.01)

(58) Field of Classification Search
None
See application file for complete search history.

(56) References Cited

U.S. PATENT DOCUMENTS

| | | | |
|---|---|---|---|
| 6,596,476 B1 * | 7/2003 | Lesniewski | C07K 14/005 435/5 |
| 7,658,911 B2 | 2/2010 | Dambinova | |
| 8,084,225 B2 | 12/2011 | Dambinova | |
| 2006/0257943 A1 | 11/2006 | Dambinova | |
| 2010/0210816 A1 | 8/2010 | Dambinova | |
| 2012/0083586 A1 | 4/2012 | Dambinova | |

FOREIGN PATENT DOCUMENTS

| | | |
|---|---|---|
| RU | 2112243 C1 | 5/1998 |
| RU | 2123704 C1 | 12/1998 |
| WO | WO-200212892 A2 | 2/2002 |

OTHER PUBLICATIONS

Lederman et al., "A single amino acid substitution in a common African allele of the CD4 molecule ablates binding of the monoclonal antibody, OKT4" Mol Immunol. Nov. 1991; 28(11):1171-81 (Year: 1991).*
Harlow, E. and Lane, D., Antibodies: A Laboratory Manual (1988) Cold Spring Harbor Laboratory Press, Cold Spring Harbor, NY, pp. 23-26 (Year: 1988).*
Colman et al. "Effects of amino acid sequence changes on antibody-antigen interactions", Research in Immunology, 1994; 145(1): 33-36 (Year: 1994).*
Dambinova SA, Bettermann K, Glynn T, Tews M, Olson D, Weissman JD, Sowell RL. Diagnostic potential of the NMDA receptor peptide assay for acute ischemic stroke. PLoS One 2012.
Dambinova SA, et al. Blood test detecting autoantibodies to N-methyl-D-aspartate neuroreceptors for evaluation of patients with transient ischemic attack. Clin Chem 2003.

\* cited by examiner

Primary Examiner — Bao Thuy L Nguyen
Assistant Examiner — Ellen J Marcsisin
(74) Attorney, Agent, or Firm — Dmitry S. Kryndushkin (57) ABSTRACT

The invention relates to diagnostics, namely to a reagent kit, a rapid method and a device for detecting the fact of chronic, ischemia-linked brain pathology. A special feature of the invention is the use of an immunoactive hybrid peptide produced as a product of two fragments of the NMDA neuroreceptor subunits. A device is described that allows quick and convenient testing of autoantibodies in the patient's blood that recognize the hybrid peptide. The method of detection of autoantibodies is based on the principle of lateral flow immunochromatography. The invention can be used for prophylactic medical examination (screening of chronic ischemia-linked brain lesions), to detect decompensated chronic cerebral ischemia at the prehospital stage by general practitioners or neurologists, as well as in neurosurgery and sports medicine for diagnostics of delayed cerebral ischemia in persons with craniocerebral injury.

12 Claims, 2 Drawing Sheets
Specification includes a Sequence Listing.

DIAGNOSTIC REAGENT KIT FOR DETECTING CHRONIC BRAIN PATHOLOGIES OF ISCHEMIC GENESIS

SEQUENCE LISTING

The instant application contains a Sequence Listing which has been filed electronically under name "Sequence_listing" on Dec. 6, 2018 in ASCII format and contains 24 kB.

FIELD OF THE INVENTION

The invention relates to diagnostic aids, namely, a method, an apparatus and a reagent kit for rapid detection of chronic brain conditions of mammals, in particular, chronic ischemia, endotoxic and cytotoxic edema (brain edema) developing in vascular and traumatic brain lesions, as well as risk of recurrent ischemic events. The invention can be used for prophylactic medical examination or primary examination of patients with a craniocerebral trauma, a stroke or a microstroke in history, and will enable to carry out most optimal therapy measures in neurology, traumatology and sports medicine.

BACKGROUND OF THE INVENTION

Stroke, as well as other acute and chronic pathologies of the brain of ischemic genesis, represent a serious threat to the health and life of people. The importance of early and highly specific diagnostics of these conditions cannot be overestimated; the rate, severity and other parameters of patient recovery depend on the correct diagnosis. Ischemic stroke is especially important to diagnose in the first three to six hours from the onset of the disease for the possibility of performing thrombolytic therapy. Despite the successes achieved, there is still a necessity for new, objective means for diagnosing the risk of recurrence of the acute phase of ischemia against the background of chronic pathology, as well as the emergence of endotoxic and cytotoxic edema (brain edema) associated with them and subsequent small vessel diseases. Diagnostics of such conditions is generally based on methods of neuroimaging, such as computed tomography and magnetic resonance imaging (MRI), which are required to identify affected areas of the brain and the extent of their damage. According to some estimates, up to 40% of stroke patients in the UK can not be diagnosed in time by radiological methods due to contraindications, the condition instability or inaccessibility of equipment (Hand P J et al. (2005) *J Neurol Neurosurg Psychiatry* 76: 1525-1527). In many other countries, the problem of equipment availability is much more serious, and, consequently, the percentage of such patients is higher. A separate problem is the diagnostics and prediction of the consequences for transient ischemic attacks (TIA) or microstrokes, with symptoms lasting from one hour to 24 hours. In many cases, patients with a stroke or TIA in history, have at least one recurrent stroke recorded within a short period of time. Ignoring the TIA symptoms by the patient can result in the development of chronic brain pathologies. Despite the understanding of the role of certain factors that determine the development of recurrent or chronic strokes, such as the atherosclerosis, high blood pressure or diabetes mellitus, currently it is not possible to monitor the patient's condition with such preceding factors, especially with underlying chronic stroke, using inexpensive biochemical tests for rapid and effective risk assessment of recurrent strokes.

Several immunoactive biomarkers contemplated for the diagnosis of stroke or TIA are known from the prior art in addition to the available means of neuroimaging (Bazarian J J, et al. *PLoS One* 2014, 9, e94734; Wang K K, et al. *J Neurotrauma* 2016, 33,1270-1277; E. G. Sorokina et al., *Journal of Neurology and Psychiatry* 2010, 110, 30-35; Guaraldi F, et al. *J Clin Med* 2015, 4, 1025-1035), however none of them have yet found application in clinical practice, mainly due to lack of specificity. Similarly, at present there are no effective tools on the market for predicting the development of chronic strokes or micro-strokes. Therefore, the problem of creating a specific inexpensive rapid test for the detection of chronic ischemia remains extremely urgent, especially when in association with cerebral edema (endotoxic or cytotoxic edema). This invention has a number of properties necessary to solve the task, and therefore enables to expand the arsenal of tools used to detect chronic brain damages and the risk of recurrent ischemic events.

SUMMARY OF THE INVENTION

It is known that the levels of circulating blood fragments of NMDA neuroreceptors can be used as a diagnostic tool for clinical evaluation of patients with stroke or TIA in history. NMDA receptors represent a subclass of ionotropic glutamate receptors that selectively bind N-methyl-D-aspartate (NMDA). The purpose of the invention is to provide a method and a device for the rapid and convenient detection of chronic brain conditions of ischemic genesis in mammals, in particular the risk of recurrent stroke or micro-stroke, delayed chronic ischemia associated with brain edema, with vascular or traumatic brain lesions leading to death of the nervous tissue cells. To solve this object, a hybrid peptide formed under pathological conditions in the form of a single fragment of two fragments of subunits of NMDA neuroreceptor subunits was obtained and tested experimentally (the possibility of the formation of such hybrids was described in the application WO/2002/012892).

A special feature of this invention is that pathological antibodies produced to hybrid fragments of NMDA neuroreceptors are used as a diagnostic marker. Determination of the level of antibodies for intrinsic protein fragments (autoantibodies) is preferable for chronic pathologies, since the effective formation of antibodies occurs in response to the repeated emergence of the antigen in the bloodstream. The level of specific autoantibodies to NMDA neuroreceptors will correlate with the severity and extent of damage to the brain structures. In this invention, the hybrid peptide is generated from two different antigenic fragments and therefore enables to detect antibodies to two different subunits of the NMDA receptor.

One of the embodiments of the invention includes a reagent kit (a set of reagents) for aiding in diagnosis of a chronic, ischemia-linked brain pathology in a mammal, comprising: a hybrid peptide having at least 90% identity over its entire length with the sequence of SEQ ID NO:1 (indicated in the Sequence Listing section), wherein the hybrid peptide is immobilized on a solid carrier; and a reagent for determining the presence of autoantibodies to said hybrid peptide in a biological fluid of the mammal, wherein the reagent has a specific binding affinity for mammalian immunoglobulins.

Thus, the hybrid peptide of this invention includes both the sequence of SEQ ID NO:1 and sequences sufficiently close to SEQ ID NO:1, and comprising amino acid inserts, replacements or deletions, that do not disturb or almost do not disturb the functional properties of the hybrid polypeptide, such as affinity for autoantibodies recognizing the NMDA receptor subunits. Blood, blood plasma, blood serum, cerebrospinal fluid, saliva, sweat, respiratory vapors or other body fluids that contain antibodies can be used as a biological fluid of a mammal. Examples of chronic pathologies of the brain of ischemic origin are chronic ischemia, recurrent and delayed strokes or micro-strokes.

In a preferred embodiment, the reagent for determining the presence of autoantibodies is an agent that can specifically bind to a constant region of mammalian antibody molecules conjugated to a visualization agent. An example of such an agent is protein A isolated from the surface of the cell wall of Staphylococcus aureus, and having a high affinity for the constant region of IgG heavy chain (Fc domain). Additionally, such an agent may be a fragment of an antibody recognizing the constant region of the heavy chain of IgG. To facilitate subsequent detection on the test strip in a preferred embodiment of the invention, such agent is conjugated to a visualization agent. The conjugation preferably occurs through the formation of a covalent bond between the two agents, but can be implemented in the other way, provided that a stable functional complex is formed. The visualization agent can be a gold nanoparticle, an organic dye, a magnetic nanoparticle, a carbon nanotube, or a fluorescent nanocrystal.

In a preferred embodiment of the invention, the solid carrier on which the hybrid peptide is immobilized is a cellulose nitrate membrane.

Some embodiments of the invention also include a diagnostic test strip for detection of chronic, ischemia-linked brain pathology in a mammal, having at least three zones configured to be in fluid communication with one another and arranged consequently, namely, a sample application zone, a reaction zone and a detection zone, wherein the sample application zone is capable of absorbing a biological fluid of a mammal and directing it to the reaction zone and the detection zone under the action of capillary forces; the detection zone comprises a test line on which a hybrid peptide is immobilized having at least 90% identity over its entire length with the sequence of SEQ ID NO:1; the reaction zone located between the sample application zone and the detection zone comprises a reagent for determining the presence of autoantibodies to said hybrid peptide in said mammalian biological fluid, wherein the reagent has a specific binding affinity for mammalian immunoglobulins.

In a preferred embodiment of the invention, a reagent for determining the presence of autoantibodies is an agent that can specifically bind to a constant region of mammalian antibody molecules, conjugated to a visualization agent, and the visualization agent may be a gold nanoparticle, an organic dye, a magnetic nanoparticle, a carbon nanotube, or a fluorescent nanocrystal.

Some embodiments of the invention also include a method for identification of mammal patients with chronic, ischemia-linked brain pathologies, comprising: sampling a biological fluid from a mammal; applying said biological fluid sample to the diagnostic test strip according to this invention into the sample application zone; determining the presence of a chronic, ischemia-linked brain pathology in said mammal when the visualization agent is detected on the test line in the detection zone of the diagnostic test strip. In a preferred embodiment of the invention, the presence of a visualization agent on the test line is determined within 15 minutes or less after application of the biological fluid sample to the diagnostic test strip.

The technical result of this invention is that this invention helps to solve the problem of rapid and objective assessment of the condition of a patient with chronic brain lesion of ischemic origin and suspected recurrent stroke. A new hybrid peptide formed by fusion of two fragments of subunits of NMDA neuroreceptors with antigenic potentials was isolated, analyzed and tested. A device is described that allows quick and convenient testing of autoantibodies in the patient's blood and recognizing a hybrid peptide. The presence of such antibodies indicates the presence of certain structural lesions of the brain and serves as an indicator of the massive death of cells of the nervous tissue. The said approach expands the available toolkit used for prophylactic medical examination or primary examination of patients with a craniocerebral trauma, a stroke or a micro-stroke in history, and will enable to carry out most optimal treatment measures.

TERMS AND DEFINITIONS

For better understanding of this invention, some terms used herein are set forth below.

In the description of this invention, the terms "includes" and "including" are deemed as meaning "includes, among other things". These terms are not intended to be interpreted as "consists only of".

The term "antibody" is equivalent to the term "immunoglobulin" and means glycoprotein formed in response to administration of bacteria, viruses or other antigens to a mammalian organism, said glycoprotein consists of two heavy (H) chains and two light (L) chains connected by disulfide bonds. Each heavy chain consists of a variable region of the heavy chain (VH) and a constant region of the heavy chain. The constant region of the heavy chain consists of three domains—CH1, CH2 and CH3. Each light chain consists of a light chain variable region (VL) and a light chain constant region. The light chain constant region consists of one CL domain. The VH and VL regions can be further subdivided into hypervariable regions, referred to as regions determining complementarity (H-CDR and L-CDR) separated by more conservative regions. The variable regions of the heavy and light chains contain a binding domain that interacts with the antigen (i.e., the antigen-binding part of the antibody). The constant regions of heavy chains have sufficiently conservative amino acid sequences with a high degree of homology for all antibody molecules of the same class. The constant regions of the immunoglobulin molecule may comprise different combinations of domains from the constant regions of heavy and/or light chains; in some embodiments, the constant region should be understood as the Fc region of an immunoglobulin molecule, which consists of a dimer formed by CH2 and CH3 domains of two heavy chains. The Fc region mediates the effector functions of the antibody, that is, the interaction of the immunoglobulin molecule with tissues or host factors, including various cells of the immune system (e.g., effector cells). The term "autoantibodies" in this specification denotes antibody molecules generated in the mammalian organism in response to antigens formed from intrinsic organism proteins (autoantigens). Autoantibodies can be produced in response to autoantigens that are normally absent in the bloodstream, for example, to hybrid fragments of neuroreceptors, or in response to fusion proteins or peptides formed by the fusion of two or more protein fragments.

A reagent that has an affinity for immunoglobulins can be any chemical capable of specifically binding to immunoglobulins and forming a new complex entity. Wherein this reagent should not inhibit the binding of immunoglobulins to their specific antigens (antibody-antigen reaction).

The term "percent identity of two sequences" used herein is determined by the number of positions of identical amino acids in these two sequences, taking into account the number of gaps and length of each gap that must be entered for optimal matching of two sequences by alignment. The percent identity is equal to the number of identical amino acids in these positions, taking into account the sequence alignment divided by the total number of positions, and multiplied by 100. The percent identity of the two amino acid sequences can be determined using the free program NCBI Protein BLAST (https://blast.ncbi.nlm.nih.gov/).

Unless otherwise specified, the technical and scientific terms in this application have standard meanings, generally accepted in the scientific and technical literature.

BRIEF DESCRIPTION OF THE FIGURES

FIG. 1. Simplified structure of a diagnostic test strip in a plastic casing. 1—a patch filter configured to receive a sample of a biological fluid, 2—a patch with a detection reagent forming a reaction zone, 3—a nitrocellulose membrane forming a detection zone, 4—an adsorbent patch, 5—a well for sample application, 6—a test line formed by the immobilized hybrid peptide, 7—a control line formed by immobilized antibodies that recognize constant regions of antibody molecules, 8—a housing of the plastic cassette covering the diagnostic test strip.

FIG. 2. Results of rapid diagnostics of chronic brain pathology after cases of mild craniocerebral injuries. Patient 1—the left part of the figure (A), Patient 2—the right part of the figure (B). The level of autoantibodies in chronic cerebral ischemia was determined using the diagnostic test strip according to the present invention (upper part of the figure). Formation of cytotoxic edema was confirmed by MRI in both patients (lower part of the figure). Designation: 11—control line, 12—test line.

DETAILED DESCRIPTION OF THE INVENTION

The key aspect of the pathogenesis of ischemic stroke is neurotoxicity and immunoexcitotoxicity, which is a cascade of pathobiochemical changes that can result in irreversible damage of the nervous tissue by the apoptosis mechanism. For example, a lack of oxygen and glucose intake that is characteristic of ischemia can cause disorder of cellular ion pumps (which represent ionotropic glutamate receptors) and excessive intake of Na+ ions into the cell, which causes an increase in intracellular osmotic pressure and, accordingly, excessive water entry into the cell. This causes the formation of cytotoxic edema of the brain. At the same time, the death of brain cells results in the release of molecules specific to the central nervous system (CNS), for example, peptide fragments of neuroreceptors, into the patient's biological fluids. These fragments penetrate through the blood-brain barrier and enter the blood of the patient, where they can be registered. Applicants have found that significant amounts of NMDA neuroreceptor fragments appear in ischemic attacks that are specific for the region of lesion with the endogenous or cytotoxic edema. Neurotoxicity activates serine proteases that cleave NMDA receptors into short peptides some of which have immune activity. In severe or chronic lesions of the nervous tissue, the concentration of such immunoactive peptides becomes high enough to initiate an autoimmune response—production of autoantibodies to these peptides—after entering into the bloodstream. Thus, both fragments of NMDA neuroreceptors and autoantibodies to them can serve as markers of death of neural tissue cells (apoptosis). Effective production of autoantibodies requires a constant influx of immunoactive hybrid fragments of NMDA receptors into the bloodstream and can occur asymptomatically in individuals with preceding factors (atherosclerosis, hypertension, diabetes) (Gonzalez-Garcia et al. *J Neurol Sci.* 2017; 375:324-330). It was revealed that the detected concentrations of NMDA of autoantibodies appear in the blood on the day 3-7 after the peptide fragments enter the blood (Dambinova S et al., *Clin Chem,* 2003 October; 49 (10): 1752-62). Along with this, autoantibodies persist in the bloodstream for a long time (from several weeks to months), and therefore they are potentially a more reliable and convenient indicator of the presence of pathology.

Determination of the presence in the blood of autoantibodies to NMDA neuroreceptors can be used for operative examination of patients with suspected stroke or TIA, as well as for evaluation of symptomatic TIA. The most effective production of autoantibodies occurs in case of a cytotoxic edema formation, when irreversible death of the nervous tissue cells occurs by apoptosis. In this case, there is a high probability of recurrent ischemic attacks, as well as the development of chronic ischemia. Currently, the cytotoxic edema is diagnosed only through diffusion-weighted image, which requires time, considerable instrumental resources and financial expenses. This invention describes the development of a device (diagnostic test strip) for predicting significant lesions of the neural tissue by detecting autoantibodies to NMDA neuroreceptors in the blood of patients using lateral flow immunochromatography.

A key aspect of creating such a device is the choice of antigen for effective and specific detection of autoantibodies. The authors of the invention analyzed various fragments of NMDA neuroreceptors circulating in the blood of patients with significant lesions of nerve tissue, and also the ability of these fragments to elicit an autoimmune response was analyzed. This ability is determined by the degree of similarity of peptide epitopes of NMDA fragments with other protein epitopes that are recognized by the immune system of the mammalian organism and are not perceived as foreign. In addition, the immunogenicity of the peptide is determined by its affinity for the receptors of the major histocompatibility complex; such affinity enables to induce a T-cell immune response and the formation of IgG antibodies to peptides. The procedure for the search and analysis of peptide fragments of neuroreceptors in the blood of patients was described by Dambinova S et al., Biomarkers for Traumatic Brain Injury, 2012, Royal Society of Chemistry (SN-978-1-84973-389-2), p. 66-86. In brief, protein fragments isolated from synaptic membranes of the cerebral cortex were used to produce polyclonal antibodies. Further, these antibodies were used to screen plasma or serum of patients with chronic brain pathologies. Affinity purified peptides from plasma of patients were identified using mass spectrometry methods. Then, the identified peptides related to fragments of glutamate receptors were synthesized and verified for effective binding to IgG antibodies isolated from the blood of patients. Thus, the most immunogenic peptides were selected.

It was revealed that peptide fragments of two subunits of NMDA neuroreceptors, namely, the subunits NR2A (product of the GRIN2A gene) and NR2B (product of the GRIN2B gene) in different concentrations, can be found in the blood of patients with significant lesions of the nervous tissue. Moreover, the presence in the blood of patients of certain hybrid peptides resulting from the fusion of smaller peptides formed from NR2A and NR2B was unexpectedly found. Such hybrid peptides are often more immunogenic than peptides derived from only one of the subunits, since the fusion of the two peptides from different subunits can result in the formation of neoantigens. To create a simple, effective and specific test system for the detection of autoantibodies, the applicants isolated, purified and analyzed various hybrid peptides present in the blood of patients with chronic brain pathologies. In particular, a hybrid peptide constructed by combining two regions of the NR2A and NR2B subunits, having a significant antigenic potential, was selected. The resulting peptide has the amino acid sequence of SEQ ID NO:1 (provided in the Sequence listing). Thus, this peptide can serve to determine the presence of autoantibodies in both NR2A and NR2B fragments.

The following examples are provided for the purpose of disclosing the characteristics of this invention and should not be considered as in any way limiting the scope of the invention.

The key parameters of the test system for the NMDA autoantibody will be specificity, minimum level of detection of autoantibodies, ease of use and interpretation of the result, cost, and reliability. The optimal level of these parameters can be obtained by implementing a test system based on lateral flow immunochromatography. In this case, a diagnostic test strip is used to determine the autoantibodies, which has at least three zones arranged in series, namely the sample application zone, the reaction zone and the detection zone; wherein the sample application zone which is initially dry, is capable of absorbing the biological fluid of the mammal and directing it to the reaction zone and the detection zone under the action of capillary forces. Various embodiments of such a design are known to those skilled in the art and can be used in this invention. For example, several drops of freshly sampled patient blood (20-80 µl) can be used as a sample. The sample is placed in the sample application zone, wherein the fluid migrates through a special patch filter to the reaction zone. The material of the special patch can be chosen to filter the blood and optimize the background signal in ways known to those skilled in the art, for example, using glass fiber materials. The reaction zone contains an agent capable of specifically binding a constant region of immunoglobulin antibody molecules, wherein this agent is conjugated to a visualization agent and is able to migrate under the action of capillary forces to the detection zone after binding to the immunoglobulin molecule. In case of chronic brain lesions, there is a constant production of fragments of NMDA neuroreceptors and their subsequent entry into the bloodstream. This results in the development of a mature immune response to immunogenic peptides with the formation of class G immunoglobulins (IgG) in the patient's blood. Therefore, in a preferred embodiment of the invention, an agent capable of specifically binding a constant region of IgG antibody molecules is used in the reaction zone. Such an agent, for example, can be protein A isolated from the surface of the cell wall of Staphylococcus aureus and having a high affinity for the constant portion of the heavy chain of IgG. For the convenience of detection, in a preferred embodiment of the invention, protein A was conjugated to the visualization agent by methods known to those skilled in the art. A substance capable of emitting detectable radiation, or in which emission of detectable radiation can be caused (for example, by radioactive decay, chemical reaction, fluorescence excitation, spin resonance excitation, etc.) can be used as a visualization agent. In various embodiments, such an agent may be a gold nanoparticle, an enzyme (e.g. horseradish peroxidase), an organic dye or a fluorescent nanocrystal (quantum dot), as well as other similar agents known to those skilled in the art. Visualization of the signal in the detection zone can occur under daylight illumination of a wide spectrum or through the use of narrow spectral sources. In a preferred embodiment of the invention, protein A was conjugated to a streptavidin molecule with a maleimid functional group; in addition, commercially available biotinylated gold nanoparticles were used. As a result, the final conjugation "protein A—gold nanoparticle" was performed with the use of high-affinity interaction of biotin and streptavidin.

The "autoantibody IgG—protein A—gold nanoparticle" complexes formed in the reaction zone migrate further to the detection zone under the action of capillary forces. In a preferred embodiment of the invention, the detection zone is a cellulose nitrate membrane with pores sufficient to pass this complex. Examples of such membranes are known to those skilled in the art. In some embodiments, membranes from the following manufacturers were used: Sartorius (CN95, CN 140), Millipore (HF 90, HF 120, HF 180) or MDI (mdi70, mdi10 µ). In a preferred embodiment of the invention, the membrane comprises at least two lines—the test and control lines, preferably arranged perpendicular to the flow of the liquid. The test line is formed by immobilization on the membrane of a selected hybrid peptide with the sequence of SEQ ID NO:1, or at least by 90% identical thereto. Various methods known to those skilled in the art can be used to immobilize a peptide on a membrane. In one embodiment, immobilization on the membrane was performed by conjugation of the peptide with bovine serum albumin (BSA). The hybrid peptide can be conjugated to BSA using a maleimid functional group using a commercially available maleimide-BSA combination. Then, the peptide-BSA complex was directly applied to the membrane near the test line and attached to the membrane during drying process.

Figure 1:
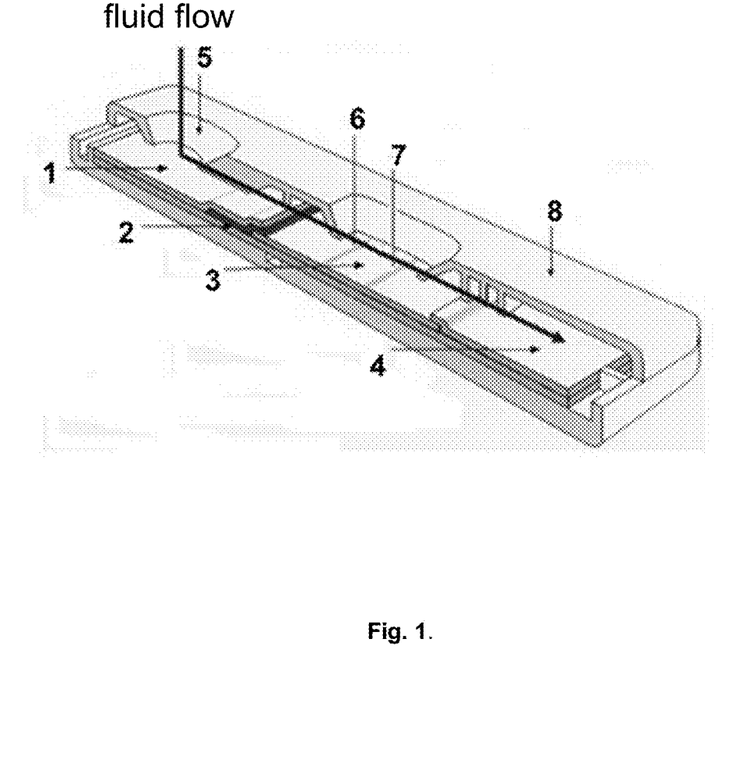

The control line is located further from the test line along the flow of the liquid and is formed by immobilization on the membrane of polyclonal anti-IgG antibodies by methods known to those skilled in the art. The "autoantibody IgG—protein A—gold nanoparticle" complex migrating from the reaction zone can first interact with the immobilized hybrid peptide, provided that the autoantibody has an affinity for this peptide. Unbound complexes migrate further to the control line, where immobilized anti-IgG antibodies are bound to these complexes. Accordingly, when only the control line has appeared, the test result is considered negative. The visualization of binding will be performed using the visualization agent, wherein the nature of the visualization agent will determine a method of detection. In a preferred embodiment of the invention, the gold nanoparticles used have good optical properties; when bound on a line and illuminated by daylight, they stain the line a dark golden color and enable to detect visually, without the use of additional equipment. The intensity of the signal will be proportional to the concentration of specific antibodies to the peptide in the sample. Finally, at the end of the detection zone, there is an adsorbent patch that maintains fluid flow along the membrane from the sample application zone to the detection zone and prevents counter-flow. A simplified structure of the diagnostic test strip in one of the embodiments of the invention is presented in FIG. 1.

The described embodiment of the invention enables to perform semiquantitative analysis of the content of autoantibodies specific for the immobilized peptide. The intensity and the rate of manifestation of the test line will be determined by the concentrations of antibodies in the sample and can be compared with the color of the lines on a reference chart specially designed for a specific set of reagents. The reference chart can be constructed by titration of a sample of specially prepared polyclonal antibodies to a hybrid peptide.

EXAMPLES OF USE OF THE INVENTION

Example 1

Result of determining antibodies to a hybrid peptide by instant diagnostics in chronic cerebral ischemia (with confirmed cytotoxic edema).

A woman, 77 years old, admitted to the neurological department No. 1 of the Pavlov First Saint Petersburg State Medical University (PFSPSMU) with complaints after a mild craniocerebral injury. Risk factors in the form of hypertension, type 2 diabetes, and advanced atherosclerosis were identified. Neurological status: 1) Moderate cognitive impairment; 2) Bilateral pyramidal insufficiency; 3) Radicular syndrome of L4-L5 on the right; 4) Polyneuropathic syndrome with shortening of vibration sensitivity and loss of Achilles tendon reflexes.

Figure 2:
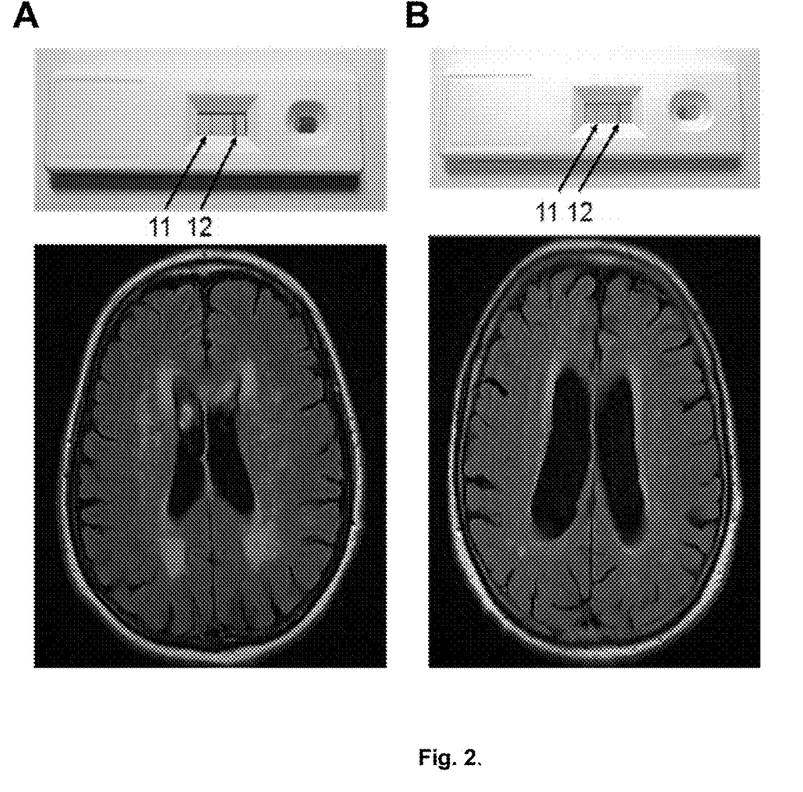

A diagnostic rapid test was performed using the test strip of this invention, as well as a brain MRI scan in the T2 FLAIR mode (FIG. 2A). In the MRI images, a cytotoxic edema was detected (manifested as light areas). The diagnostic rapid test showed the presence of two lines (FIG. 2A).

Example 2

Result of determining antibodies to a hybrid peptide by instant diagnostics in chronic cerebral ischemia (with confirmed cytotoxic edema).

A woman, 83 years old, admitted the neurological department No. 1 of the PFSPSMU with complaints of unsteady gait, stiffness in limb movements, periodic sensations of blackout, dizziness, trembling in the whole body, pedal edema. Previously, she was hospitalized in the PFSPSMU with a diagnosis of dyscirculatory encephalopathy of degree III, a syndrome of vascular Parkinson disease. Risk factors in the form of hypertension, and advanced atherosclerosis were identified. Neurological status: 1) mild cognitive impairment; 2) pseudobulbar syndrome; 3) parkinsonian syndrome; 4) bilateral pyramidal insufficiency; 5) disorder of statics and dynamics in the lumbar spine.

A diagnostic rapid test was performed using the test strip of this invention, as well as a brain MRI scan in the T2 FLAIR mode (FIG. 2B). In the MRI images, a cytotoxic edema was detected (manifested as light areas and spots). The diagnostic rapid test showed the presence of two lines (FIG. 2B).

Example 3

Pilot study of patients of the Saint Petersburg State Medical University using diagnostic test strips of this invention.

The study enrolled 10 subjects with an established working diagnosis of dyscirculatory encephalopathy/chronic disorder of cerebral circulation (CDCC), which according to the International Classification of Diseases corresponds to the code 167 (167.2 Cerebral atherosclerosis, 167.4 Hypertensive encephalopathy, 167.8 Other specified lesions of the cerebral vessels). The diagnosis was confirmed by clinical (neurological examination), neuro-psychological (MMSE and FAB scales) and instrumental research methods (neuroimaging, duplex scanning); 3 men and 7 women took part in the study, the mean age was 68.3 years. Magnetic resonance imaging (MRI) in the modes of T1, T2, T2 FLAIR, DWI, GRE, as well as other examination methods aimed at searching potential risk factors for cerebral circulation disorders, were performed to all participants of the study. Thus, atherosclerosis of brachiocephalic and cerebral arteries was detected in 7 patients, hypertensive disease was revealed in 5 patients, diabetes mellitus in 2 patients, and arrhythmias in 2 patients. A combination of three risk factors was diagnosed in two patients. The control group consisted of 12 relatively healthy volunteers, selected taking into account the mean age identical to the mean age of the test group of patients.

When admission to the hospital, capillary blood was sampled from the patients, 80 µl of the sample was placed in a special rapid test window, and 10 µl of phosphate buffer was added. Within 30 minutes (an average of 15 minutes), the development of an immunochromatographic reaction was observed in the form of the appearance on the rapid test screen of a control C-line and a test T-line. In eight out of ten patients with a diagnosis of chronic disorder of cerebral circulation/dyscirculatory encephalopathy, the rapid test showed a positive result. In the control group of 12 patients, the test line appeared only in one case. Thus, preliminary tests of the diagnostic test strips of this invention demonstrated the sensitivity of about 80% and the specificity of about 93%.

Despite the fact that the invention has been described with reference to the disclosed variants of the invention embodiments, it should be obvious to the those skilled in the art that the specific, detailed described experiments are shown for the purpose of illustrating this invention only, and should not be considered as those that in any way confine the scope of the invention. It should be understood that the embodiment of various modifications are possible without deviation from the essence of this invention.

The invention claimed is:

1. A reagent kit for aiding in diagnosis of a chronic, ischemia-linked brain pathology in a mammal, comprising:
   a) a hybrid peptide having the amino acid sequence of SEQ ID NO:1, wherein the hybrid peptide is immobilized on a solid carrier;
   b) a reagent for determining the presence of autoantibodies to said hybrid peptide in a biological fluid of the mammal, wherein the reagent has a specific binding affinity for mammalian immunoglobulins.

2. The reagent kit according to claim 1, wherein the biological fluid is blood, blood plasma, serum, cerebrospinal fluid, saliva or sweat.

3. The reagent kit according to claim 2, wherein the reagent for determining the presence of autoantibodies is a binding agent conjugated to a visualization agent, wherein the binding agent specifically binds to a constant region of mammalian antibody molecules.

4. The reagent kit according to claim 3, wherein the visualization agent is a gold nanoparticle, an organic dye, or a fluorescent nanocrystal.

5. The reagent kit according to claim 1, wherein the chronic ischemia-linked brain pathology is a disease state selected from the following list: chronic ischemia, chronic transient ischemic attacks, repeated strokes or microstrokes, and cerebral edema.

6. The reagent kit according to claim 5, wherein the solid carrier is a cellulose nitrate membrane.

7. A diagnostic test strip for detection of chronic, ischemia-linked brain pathology in a mammal, having at least three zones configured to be in fluid communication with one another and arranged consecutively, namely, a sample application zone, a reaction zone and a detection zone, wherein the sample application zone is capable of absorbing a biological fluid of a mammal and directing it to the reaction zone and the detection zone under the action of capillary forces;
   the detection zone comprises a test line on which a hybrid peptide having the amino acid sequence of SEQ ID NO:1 is immobilized;
   the reaction zone located between the sample application zone and the detection zone comprises a reagent for determining the presence of autoantibodies to said hybrid peptide in said mammalian biological fluid, wherein the reagent has a specific binding affinity for mammalian immunoglobulins.

8. The diagnostic test strip according to claim 7, wherein the biological fluid is blood, blood plasma, serum, cerebrospinal fluid, saliva, or sweat.

9. The diagnostic test strip according to claim 8, wherein the reagent for determining the presence of autoantibodies is a binding agent conjugated to a visualization agent, wherein the binding agent specifically binds to a constant region of mammalian antibody molecules.

10. The diagnostic test strip according to claim 9, wherein the visualization agent is a gold nanoparticle, an organic dye or a fluorescent nanocrystal.

11. A method of identification of mammal patients with chronic, ischemia-linked brain pathologies, comprising:
   (a) sampling a biological fluid from a mammal;
   (b) applying said biological fluid sample into the sample application zone of a diagnostic test strip according to claim 7;
   (c) determining the presence of a chronic, ischemia-linked brain pathology in said mammal when the visualization agent is detected on the test line in the detection zone of the diagnostic test strip.

12. The method according to claim 11, wherein determination of the presence of the visualization agent on the test line occurs within 15 minutes or less after applying a biological fluid sample to the diagnostic test strip.

* * * * *

SEQUENCE LISTING

```
<160> NUMBER OF SEQ ID NOS: 3

<210> SEQ ID NO 1
<211> LENGTH: 36
<212> TYPE: PRT
<213> ORGANISM: Artificial sequence
<220> FEATURE:
<223> OTHER INFORMATION: hybrid peptide

<400> SEQUENCE: 1
```

```
Ala Ala Val Leu Asn Tyr Lys Ala Gly Arg Asp Glu Gly Cys Lys Leu
1               5                   10                  15

Val Thr Ile Leu Thr Gly Ile Cys His Asn Glu Lys Asn Glu Val Met
            20                  25                  30

Ser Ser Gln Leu
        35

<210> SEQ ID NO 2
<211> LENGTH: 1281
<212> TYPE: PRT
<213> ORGANISM: Homo sapiens
<220> FEATURE:
<223> OTHER INFORMATION: Glutamate receptor, ionotropic, N-methyl D-
      aspartate 2A

<400> SEQUENCE: 2

Met Gly Arg Val Gly Tyr Trp Thr Leu Leu Val Leu Pro Ala Leu Leu
1               5                   10                  15

Val Trp Arg Gly Pro Ala Pro Ser Ala Ala Glu Lys Gly Pro Pro
            20                  25                  30

Ala Leu Asn Ile Ala Val Met Leu Gly His Ser His Asp Val Thr Glu
            35                  40                  45

Arg Glu Leu Arg Thr Leu Trp Gly Pro Glu Gln Ala Ala Gly Leu Pro
50                  55                  60

Leu Asp Val Asn Val Val Ala Leu Leu Met Asn Arg Thr Asp Pro Lys
65                  70                  75                  80

Ser Leu Ile Thr His Val Cys Asp Leu Met Ser Gly Ala Arg Ile His
                85                  90                  95

Gly Leu Val Phe Gly Asp Asp Thr Asp Gln Glu Ala Val Ala Gln Met
            100                 105                 110

Leu Asp Phe Ile Ser Ser His Thr Phe Val Pro Ile Leu Gly Ile His
            115                 120                 125

Gly Gly Ala Ser Met Ile Met Ala Asp Lys Asp Pro Thr Ser Thr Phe
        130                 135                 140

Phe Gln Phe Gly Ala Ser Ile Gln Gln Gln Ala Thr Val Met Leu Lys
145                 150                 155                 160

Ile Met Gln Asp Tyr Asp Trp His Val Phe Ser Leu Val Thr Thr Ile
                165                 170                 175

Phe Pro Gly Tyr Arg Glu Phe Ile Ser Phe Val Lys Thr Thr Val Asp
            180                 185                 190

Asn Ser Phe Val Gly Trp Asp Met Gln Asn Val Ile Thr Leu Asp Thr
        195                 200                 205

Ser Phe Glu Asp Ala Lys Thr Gln Val Gln Leu Lys Lys Ile His Ser
    210                 215                 220

Ser Val Ile Leu Leu Tyr Cys Ser Lys Asp Glu Ala Val Leu Ile Leu
225                 230                 235                 240

Ser Glu Ala Arg Ser Leu Gly Leu Thr Gly Tyr Asp Phe Phe Trp Ile
                245                 250                 255

Val Pro Ser Leu Val Ser Gly Asn Thr Glu Leu Ile Pro Lys Glu Phe
            260                 265                 270

Pro Ser Gly Leu Ile Ser Val Ser Tyr Asp Asp Trp Asp Tyr Ser Leu
        275                 280                 285

Glu Ala Arg Val Arg Asp Gly Ile Gly Ile Leu Thr Thr Ala Ala Ser
    290                 295                 300

Ser Met Leu Glu Lys Phe Ser Tyr Ile Pro Glu Ala Lys Ala Ser Cys
305                 310                 315                 320
```

-continued

Tyr Gly Gln Met Glu Arg Pro Glu Val Pro Met His Thr Leu His Pro
            325                 330                 335

Phe Met Val Asn Val Thr Trp Asp Gly Lys Asp Leu Ser Phe Thr Glu
            340                 345                 350

Glu Gly Tyr Gln Val His Pro Arg Leu Val Val Ile Val Leu Asn Lys
            355                 360                 365

Asp Arg Glu Trp Glu Lys Val Gly Lys Trp Glu Asn His Thr Leu Ser
370                 375                 380

Leu Arg His Ala Val Trp Pro Arg Tyr Lys Ser Phe Ser Asp Cys Glu
385                 390                 395                 400

Pro Asp Asp Asn His Leu Ser Ile Val Thr Leu Glu Glu Ala Pro Phe
            405                 410                 415

Val Ile Val Glu Asp Ile Asp Pro Leu Thr Glu Thr Cys Val Arg Asn
            420                 425                 430

Thr Val Pro Cys Arg Lys Phe Val Lys Ile Asn Asn Ser Thr Asn Glu
            435                 440                 445

Gly Met Asn Val Lys Lys Cys Cys Lys Gly Phe Cys Ile Asp Ile Leu
    450                 455                 460

Lys Lys Leu Ser Arg Thr Val Lys Phe Thr Tyr Asp Leu Tyr Leu Val
465                 470                 475                 480

Thr Asn Gly Lys His Gly Lys Lys Val Asn Asn Val Trp Asn Gly Met
                485                 490                 495

Ile Gly Glu Val Val Tyr Gln Arg Ala Val Met Ala Val Gly Ser Leu
            500                 505                 510

Thr Ile Asn Glu Glu Arg Ser Glu Val Val Asp Phe Ser Val Pro Phe
            515                 520                 525

Val Glu Thr Gly Ile Ser Val Met Val Ser Arg Ser Asn Gly Thr Val
    530                 535                 540

Ser Pro Ser Ala Phe Leu Glu Pro Phe Ser Ala Ser Val Trp Val Met
545                 550                 555                 560

Met Phe Val Met Leu Leu Ile Val Ser Ala Ile Ala Val Phe Val Phe
                565                 570                 575

Glu Tyr Phe Ser Pro Val Gly Tyr Asn Arg Asn Leu Ala Lys Gly Lys
            580                 585                 590

Ala Pro His Gly Pro Ser Phe Thr Ile Gly Lys Ala Ile Trp Leu Leu
            595                 600                 605

Trp Gly Leu Val Phe Asn Asn Ser Val Pro Val Gln Asn Pro Lys Gly
    610                 615                 620

Thr Thr Ser Lys Ile Met Val Ser Val Trp Ala Phe Phe Ala Val Ile
625                 630                 635                 640

Phe Leu Ala Ser Tyr Thr Ala Asn Leu Ala Ala Phe Met Ile Gln Glu
                645                 650                 655

Glu Phe Val Asp Gln Val Thr Gly Leu Ser Asp Lys Lys Phe Gln Arg
            660                 665                 670

Pro His Asp Tyr Ser Pro Pro Phe Arg Phe Gly Thr Val Pro Asn Gly
            675                 680                 685

Ser Thr Glu Arg Asn Ile Arg Asn Asn Tyr Pro Tyr Met His Gln Tyr
    690                 695                 700

Met Thr Lys Phe Asn Gln Lys Gly Val Glu Asp Ala Leu Val Ser Leu
705                 710                 715                 720

Lys Thr Gly Lys Leu Asp Ala Phe Ile Tyr Asp Ala Ala Val Leu Asn
                725                 730                 735

Tyr Lys Ala Gly Arg Asp Glu Gly Cys Lys Leu Val Thr Ile Gly Ser
            740                 745                 750

Gly Tyr Ile Phe Ala Thr Thr Gly Tyr Gly Ile Ala Leu Gln Lys Gly
        755                 760                 765

Ser Pro Trp Lys Arg Gln Ile Asp Leu Ala Leu Leu Gln Phe Val Gly
    770                 775                 780

Asp Gly Glu Met Glu Glu Leu Glu Thr Leu Trp Leu Thr Gly Ile Cys
785                 790                 795                 800

His Asn Glu Lys Asn Glu Val Met Ser Ser Gln Leu Asp Ile Asp Asn
                805                 810                 815

Met Ala Gly Val Phe Tyr Met Leu Ala Ala Met Ala Leu Ser Leu
            820                 825                 830

Ile Thr Phe Ile Trp Glu His Leu Phe Tyr Trp Lys Leu Arg Phe Cys
        835                 840                 845

Phe Thr Gly Val Cys Ser Asp Arg Pro Gly Leu Leu Phe Ser Ile Ser
    850                 855                 860

Arg Gly Ile Tyr Ser Cys Ile His Gly Val His Ile Glu Glu Lys Lys
865                 870                 875                 880

Lys Ser Pro Asp Phe Asn Leu Thr Gly Ser Gln Ser Asn Met Leu Lys
                885                 890                 895

Leu Leu Arg Ser Ala Lys Asn Ile Ser Ser Met Ser Asn Met Asn Ser
            900                 905                 910

Ser Arg Met Asp Ser Pro Lys Arg Ala Ala Asp Phe Ile Gln Arg Gly
        915                 920                 925

Ser Leu Ile Met Asp Met Val Ser Asp Lys Gly Asn Leu Met Tyr Ser
    930                 935                 940

Asp Asn Arg Ser Phe Gln Gly Lys Glu Ser Ile Phe Gly Asp Asn Met
945                 950                 955                 960

Asn Glu Leu Gln Thr Phe Val Ala Asn Arg Gln Lys Asp Asn Leu Asn
                965                 970                 975

Asn Tyr Val Phe Gln Gly Gln His Pro Leu Thr Leu Asn Glu Ser Asn
            980                 985                 990

Pro Asn Thr Val Glu Val Ala Val Ser Thr Glu Ser Lys Ala Asn Ser
        995                 1000                1005

Arg Pro Arg Gln Leu Trp Lys Lys Ser Val Asp Ser Ile Arg Gln Asp
    1010                1015                1020

Ser Leu Ser Gln Asn Pro Val Ser Gln Arg Asp Glu Ala Thr Ala Glu
1025                1030                1035                1040

Asn Arg Thr His Ser Leu Lys Ser Pro Arg Tyr Leu Pro Glu Glu Met
                1045                1050                1055

Ala His Ser Asp Ile Ser Glu Thr Ser Asn Arg Ala Thr Cys His Arg
            1060                1065                1070

Glu Pro Asp Asn Ser Lys Asn His Lys Thr Lys Asp Asn Phe Lys Arg
        1075                1080                1085

Ser Val Ala Ser Lys Tyr Pro Lys Asp Cys Ser Glu Val Glu Arg Thr
    1090                1095                1100

Tyr Leu Lys Thr Lys Ser Ser Pro Arg Asp Lys Ile Tyr Thr Ile
1105                1110                1115                1120

Asp Gly Glu Lys Glu Pro Gly Phe His Leu Asp Pro Gln Phe Val
                1125                1130                1135

Glu Asn Val Thr Leu Pro Glu Asn Val Asp Phe Pro Asp Pro Tyr Gln
            1140                1145                1150

Asp Pro Ser Glu Asn Phe Arg Lys Gly Asp Ser Thr Leu Pro Met Asn

```
                    1155                1160                1165
Arg Asn Pro Leu His Asn Glu Glu Gly Leu Ser Asn Asn Asp Gln Tyr
            1170                1175                1180
Lys Leu Tyr Ser Lys His Phe Thr Leu Lys Asp Lys Gly Ser Pro His
1185                1190                1195                1200
Ser Glu Thr Ser Glu Arg Tyr Arg Gln Asn Ser Thr His Cys Arg Ser
                1205                1210                1215
Cys Leu Ser Asn Met Pro Thr Tyr Ser Gly His Phe Thr Met Arg Ser
            1220                1225                1230
Pro Phe Lys Cys Asp Ala Cys Leu Arg Met Gly Asn Leu Tyr Asp Ile
        1235                1240                1245
Asp Glu Asp Gln Met Leu Gln Glu Thr Gly Met Thr Asn Ala Trp Leu
    1250                1255                1260
Leu Gly Asp Ala Pro Arg Thr Leu Thr Asn Thr Arg Cys His Pro Arg
1265                1270                1275                1280
Arg

<210> SEQ ID NO 3
<211> LENGTH: 1484
<212> TYPE: PRT
<213> ORGANISM: Homo sapiens
<220> FEATURE:
<223> OTHER INFORMATION: Glutamate receptor, ionotropic, N-methyl D-
      aspartate 2B

<400> SEQUENCE: 3

Met Lys Pro Arg Ala Glu Cys Cys Ser Pro Lys Phe Trp Leu Val Leu
1               5                   10                  15
Ala Val Leu Ala Val Ser Gly Ser Arg Ala Arg Ser Gln Lys Ser Pro
            20                  25                  30
Pro Ser Ile Gly Ile Ala Val Ile Leu Val Gly Thr Ser Asp Glu Val
        35                  40                  45
Ala Ile Lys Asp Ala His Glu Lys Asp Asp Phe His His Leu Ser Val
    50                  55                  60
Val Pro Arg Val Glu Leu Val Ala Met Asn Glu Thr Asp Pro Lys Ser
65                  70                  75                  80
Ile Ile Thr Arg Ile Cys Asp Leu Met Ser Asp Arg Lys Ile Gln Gly
                85                  90                  95
Val Val Phe Ala Asp Asp Thr Asp Gln Glu Ala Ile Ala Gln Ile Leu
            100                 105                 110
Asp Phe Ile Ser Ala Gln Thr Leu Thr Pro Ile Leu Gly Ile His Gly
        115                 120                 125
Gly Ser Ser Met Ile Met Ala Asp Lys Asp Glu Ser Ser Met Phe Phe
    130                 135                 140
Gln Phe Gly Pro Ser Ile Glu Gln Gln Ala Ser Val Met Leu Asn Ile
145                 150                 155                 160
Met Glu Glu Tyr Asp Trp Tyr Ile Phe Ser Ile Val Thr Thr Tyr Phe
                165                 170                 175
Pro Gly Tyr Gln Asp Phe Val Asn Lys Ile Arg Ser Thr Ile Glu Asn
            180                 185                 190
Ser Phe Val Gly Trp Glu Leu Glu Glu Val Leu Leu Leu Asp Met Ser
        195                 200                 205
Leu Asp Asp Gly Asp Ser Lys Ile Gln Asn Gln Leu Lys Lys Leu Gln
    210                 215                 220
Ser Pro Ile Ile Leu Leu Tyr Cys Thr Lys Glu Glu Ala Thr Tyr Ile
```

-continued

|     |     |     |     |     |     |     |     |     |     |     |     |
|-----|-----|-----|-----|-----|-----|-----|-----|-----|-----|-----|-----|
| 225 |     |     |     |     | 230 |     |     |     | 235 |     | 240 |
| Phe | Glu | Val | Ala | Asn | Ser | Val | Gly | Leu | Thr | Gly | Tyr |
|     |     |     |     | 245 |     |     |     |     | 250 |     |     |
| Gly | Tyr | Thr | Trp | Ile | Val | Pro | Ser | Leu | Val | Ala | Gly |
|     | 255 |     |     |     |     | 260 |     |     |     |     |     |

Phe Glu Val Ala Asn Ser Val Gly Leu Thr Gly Tyr Gly Tyr Thr Trp
                245                 250             255

Ile Val Pro Ser Leu Val Ala Gly Asp Thr Asp Thr Val Pro Ala Glu
            260                 265             270

Phe Pro Thr Gly Leu Ile Ser Val Ser Tyr Asp Glu Trp Asp Tyr Gly
        275              280              285

Leu Pro Ala Arg Val Arg Asp Gly Ile Ala Ile Thr Thr Ala Ala
    290              295              300

Ser Asp Met Leu Ser Glu His Ser Phe Ile Pro Glu Pro Lys Ser Ser
305             310              315              320

Cys Tyr Asn Thr His Glu Lys Arg Ile Tyr Gln Ser Asn Met Leu Asn
                325              330              335

Arg Tyr Leu Ile Asn Val Thr Phe Glu Gly Arg Asn Leu Ser Phe Ser
                340              345              350

Glu Asp Gly Tyr Gln Met His Pro Lys Leu Val Ile Ile Leu Leu Asn
            355              360              365

Lys Glu Arg Lys Trp Glu Arg Val Gly Lys Trp Lys Asp Lys Ser Leu
    370              375              380

Gln Met Lys Tyr Tyr Val Trp Pro Arg Met Cys Pro Glu Thr Glu Glu
385              390              395              400

Gln Glu Asp Asp His Leu Ser Ile Val Thr Leu Glu Glu Ala Pro Phe
            405              410              415

Val Ile Val Glu Ser Val Asp Pro Leu Ser Gly Thr Cys Met Arg Asn
            420              425              430

Thr Val Pro Cys Gln Lys Arg Ile Val Thr Glu Asn Lys Thr Asp Glu
        435              440              445

Glu Pro Gly Tyr Ile Lys Lys Cys Cys Lys Gly Phe Cys Ile Asp Ile
    450              455              460

Leu Lys Lys Ile Ser Lys Ser Val Lys Phe Thr Tyr Asp Leu Tyr Leu
465              470              475              480

Val Thr Asn Gly Lys His Gly Lys Lys Ile Asn Gly Thr Trp Asn Gly
            485              490              495

Met Ile Gly Glu Val Val Met Lys Arg Ala Tyr Met Ala Val Gly Ser
        500              505              510

Leu Thr Ile Asn Glu Glu Arg Ser Glu Val Val Asp Phe Ser Val Pro
    515              520              525

Phe Ile Glu Thr Gly Ile Ser Val Met Val Ser Arg Ser Asn Gly Thr
530              535              540

Val Ser Pro Ser Ala Phe Leu Glu Pro Phe Ser Ala Asp Val Trp Val
545              550              555              560

Met Met Phe Val Met Leu Leu Ile Val Ser Ala Val Ala Val Phe Val
            565              570              575

Phe Glu Tyr Phe Ser Pro Val Gly Tyr Asn Arg Cys Leu Ala Asp Gly
        580              585              590

Arg Glu Pro Gly Gly Pro Ser Phe Thr Ile Gly Lys Ala Ile Trp Leu
    595              600              605

Leu Trp Gly Leu Val Phe Asn Asn Ser Val Pro Val Gln Asn Pro Lys
    610              615              620

Gly Thr Thr Ser Lys Ile Met Val Ser Val Trp Ala Phe Phe Ala Val
625              630              635              640

Ile Phe Leu Ala Ser Tyr Thr Ala Asn Leu Ala Ala Phe Met Ile Gln
            645              650              655

```
Glu Glu Tyr Val Asp Gln Val Ser Gly Leu Ser Asp Lys Lys Phe Gln
            660                 665                 670

Arg Pro Asn Asp Phe Ser Pro Pro Phe Arg Phe Gly Thr Val Pro Asn
            675                 680                 685

Gly Ser Thr Glu Arg Asn Ile Arg Asn Asn Tyr Ala Glu Met His Ala
            690                 695                 700

Tyr Met Gly Lys Phe Asn Gln Arg Gly Val Asp Asp Ala Leu Leu Ser
705                 710                 715                 720

Leu Lys Thr Gly Lys Leu Asp Ala Phe Ile Tyr Asp Ala Ala Val Leu
                725                 730                 735

Asn Tyr Met Ala Gly Arg Asp Glu Gly Cys Lys Leu Val Thr Ile Gly
            740                 745                 750

Ser Gly Lys Val Phe Ala Ser Thr Gly Tyr Gly Ile Ala Ile Gln Lys
            755                 760                 765

Asp Ser Gly Trp Lys Arg Gln Val Asp Leu Ala Ile Leu Gln Leu Phe
            770                 775                 780

Gly Asp Gly Glu Met Glu Glu Leu Glu Ala Leu Trp Leu Thr Gly Ile
785                 790                 795                 800

Cys His Asn Glu Lys Asn Glu Val Met Ser Ser Gln Leu Asp Ile Asp
                805                 810                 815

Asn Met Ala Gly Val Phe Tyr Met Leu Gly Ala Ala Met Ala Leu Ser
            820                 825                 830

Leu Ile Thr Phe Ile Cys Glu His Leu Phe Tyr Trp Gln Phe Arg His
            835                 840                 845

Cys Phe Met Gly Val Cys Ser Gly Lys Pro Gly Met Val Phe Ser Ile
            850                 855                 860

Ser Arg Gly Ile Tyr Ser Cys Ile His Gly Val Ala Ile Glu Glu Arg
865                 870                 875                 880

Gln Ser Val Met Asn Ser Pro Thr Ala Thr Met Asn Asn Thr His Ser
                885                 890                 895

Asn Ile Leu Arg Leu Leu Arg Thr Ala Lys Asn Met Ala Asn Leu Ser
            900                 905                 910

Gly Val Asn Gly Ser Pro Gln Ser Ala Leu Asp Phe Ile Arg Arg Glu
            915                 920                 925

Ser Ser Val Tyr Asp Ile Ser Glu His Arg Arg Ser Phe Thr His Ser
            930                 935                 940

Asp Cys Lys Ser Tyr Asn Asn Pro Pro Cys Glu Glu Asn Leu Phe Ser
945                 950                 955                 960

Asp Tyr Ile Ser Glu Val Glu Arg Thr Phe Gly Asn Leu Gln Leu Lys
                965                 970                 975

Asp Ser Asn Val Tyr Gln Asp His Tyr His His His Arg Pro His
            980                 985                 990

Ser Ile Gly Ser Ala Ser Ser Ile Asp Gly Leu Tyr Asp Cys Asp Asn
            995                 1000                1005

Pro Pro Phe Thr Thr Gln Ser Arg Ser Ile Ser Lys Lys Pro Leu Asp
            1010                1015                1020

Ile Gly Leu Pro Ser Ser Lys His Ser Gln Leu Ser Asp Leu Tyr Gly
1025                1030                1035                1040

Lys Phe Ser Phe Lys Ser Asp Arg Tyr Ser Gly His Asp Asp Leu Ile
                1045                1050                1055

Arg Ser Asp Val Ser Asp Ile Ser Thr His Thr Val Thr Tyr Gly Asn
            1060                1065                1070
```

-continued

```
Ile Glu Gly Asn Ala Ala Lys Arg Arg Lys Gln Gln Tyr Lys Asp Ser
            1075                1080                1085

Leu Lys Lys Arg Pro Ala Ser Ala Lys Ser Arg Glu Phe Asp Glu
    1090                1095                1100

Ile Glu Leu Ala Tyr Arg Arg Pro Pro Arg Ser Pro Asp His Lys
1105                1110                1115                1120

Arg Tyr Phe Arg Asp Lys Glu Gly Leu Arg Asp Phe Tyr Leu Asp Gln
                1125                1130                1135

Phe Arg Thr Lys Glu Asn Ser Pro His Trp Glu His Val Asp Leu Thr
            1140                1145                1150

Asp Ile Tyr Lys Glu Arg Ser Asp Asp Phe Lys Arg Asp Ser Val Ser
            1155                1160                1165

Gly Gly Gly Pro Cys Thr Asn Arg Ser His Ile Lys His Gly Thr Gly
    1170                1175                1180

Asp Lys His Gly Val Val Ser Gly Val Pro Ala Pro Trp Glu Lys Asn
1185                1190                1195                1200

Leu Thr Asn Val Glu Trp Glu Asp Arg Ser Gly Gly Asn Phe Cys Arg
                1205                1210                1215

Ser Cys Pro Ser Lys Leu His Asn Tyr Ser Thr Thr Val Thr Gly Gln
            1220                1225                1230

Asn Ser Gly Arg Gln Ala Cys Ile Arg Cys Glu Ala Cys Lys Lys Ala
            1235                1240                1245

Gly Asn Leu Tyr Asp Ile Ser Glu Asp Asn Ser Leu Gln Glu Leu Asp
    1250                1255                1260

Gln Pro Ala Ala Pro Val Ala Val Thr Ser Asn Ala Ser Thr Thr Lys
1265                1270                1275                1280

Tyr Pro Gln Ser Pro Thr Asn Ser Lys Ala Gln Lys Lys Asn Arg Asn
                1285                1290                1295

Lys Leu Arg Arg Gln His Ser Tyr Asp Thr Phe Val Asp Leu Gln Lys
            1300                1305                1310

Glu Glu Ala Ala Leu Ala Pro Arg Ser Val Ser Leu Lys Asp Lys Gly
            1315                1320                1325

Arg Phe Met Asp Gly Ser Pro Tyr Ala His Met Phe Glu Met Ser Ala
    1330                1335                1340

Gly Glu Ser Thr Phe Ala Asn Asn Lys Ser Ser Val Pro Thr Ala Gly
1345                1350                1355                1360

His His His His Asn Asn Pro Gly Gly Gly Tyr Met Leu Ser Lys Ser
                1365                1370                1375

Leu Tyr Pro Asp Arg Val Thr Gln Asn Pro Phe Ile Pro Thr Phe Gly
            1380                1385                1390

Asp Asp Gln Cys Leu Leu His Gly Ser Lys Ser Tyr Phe Phe Arg Gln
            1395                1400                1405

Pro Thr Val Ala Gly Ala Ser Lys Ala Arg Pro Asp Phe Arg Ala Leu
    1410                1415                1420

Val Thr Asn Lys Pro Val Val Ser Ala Leu His Gly Ala Val Pro Ala
1425                1430                1435                1440

Arg Phe Gln Lys Asp Ile Cys Ile Gly Asn Gln Ser Asn Pro Cys Val
                1445                1450                1455

Pro Asn Asn Lys Asn Pro Arg Ala Phe Asn Gly Ser Ser Asn Gly His
            1460                1465                1470

Val Tyr Glu Lys Leu Ser Ser Ile Glu Ser Asp Val
            1475                1480
```